United States Patent [19]

Pascoe

[11] Patent Number: 4,780,568

[45] Date of Patent: Oct. 25, 1988

[54] PURIFICATION OF METHACRYLIC ACID FROM AN OXYDEHYDROGENATION BY CRYSTALLIZATION

[75] Inventor: Ralph F. Pascoe, Marysville, Ohio

[73] Assignee: Ashland Oil, Inc., Ashland, Ky.

[21] Appl. No.: 113,586

[22] Filed: Oct. 19, 1987

Related U.S. Application Data

[63] Continuation-in-part of Ser. No. 682,882, Dec. 14, 1984, abandoned.

[51] Int. Cl.$^4$ .................. C07C 51/377; C07C 51/47; C07C 51/50; C07C 57/07; C07C 57/075
[52] U.S. Cl. .................................... 562/599; 562/600; 562/606
[58] Field of Search ................. 562/600, 599, 606

[56] References Cited

U.S. PATENT DOCUMENTS 4,230,888 10/1980 Pospek ........................... 562/600

FOREIGN PATENT DOCUMENTS 51-8213 1/1976 Japan ............................. 562/600

Primary Examiner—Vivian Garner
Attorney, Agent, or Firm—John F. Jones

[57] ABSTRACT

A process for separation of methacrylic acid from methacrylic acid-isobutyric acid mixtures involving the selective crystallization and removal of the methacrylic acid from said mixtures is decribed.

8 Claims, 1 Drawing Sheet

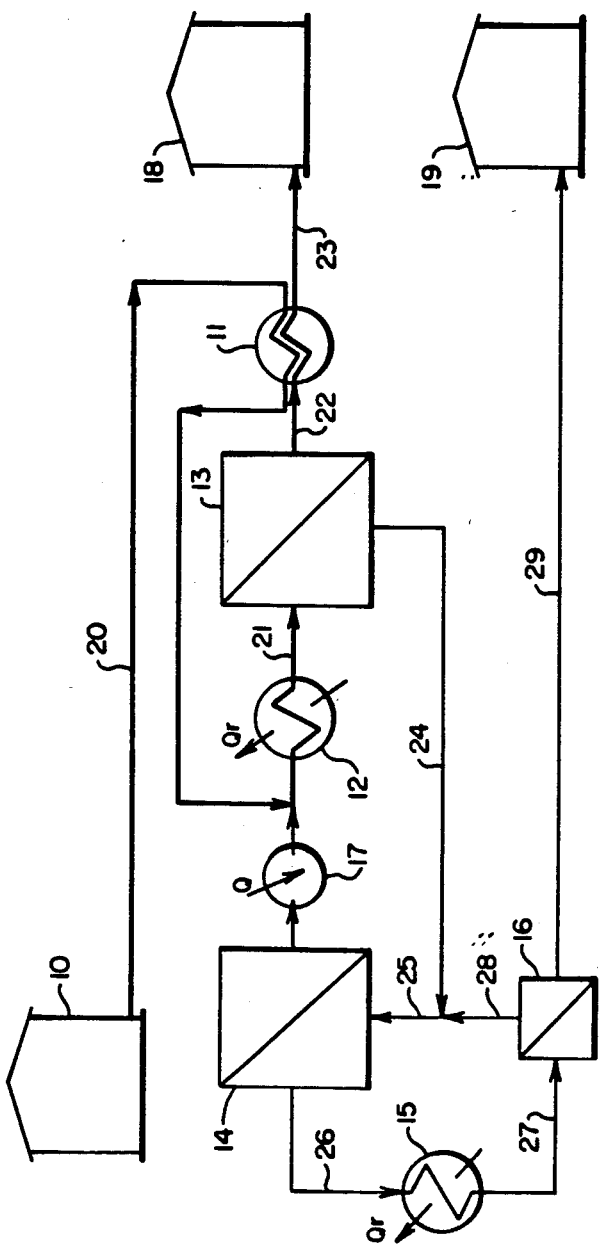

PURIFICATION OF METHACRYLIC ACID FROM AN OXYDEHYDROGENATION BY CRYSTALLIZATION

This is a continuation-in-part application based on my copending U.S. patent application Ser. No. 682,882, filed Dec. 14, 1984, now abandoned.

CROSS-REFERENCE TO RELATED PATENT APPLICATIONS

The recovery of methacrylic acid from the oxidative dehydrogenation of isobutyric acid in the form of a water-free mixture of methacrylic acid and isobutyric acid is described in my copending U.S. patent application Ser. No. 682,506, filed 12/17/84, now abandoned.

This invention relates to a process for the isolation of highly pure methacrylic acid from mixtures of methacrylic acid, isobutyric acid and other extraneous impurities and, more particularly, pertains to a crystallization process for the isolation and purification of methacrylic acid from its mixtures with isobutyric acid and other impurities; such mixtures include those which are produced in the oxydehydrogenation of isobutyric acid in the vapor phase in the presence of oxygen and a heterogeneous oxydehydrogenation catalyst.

The preparation of methacrylic acid by the oxydehydrogenation of isobutyric acid over an oxidative dehydrogenation catalyst is well known to those skilled in the art. See, for instance, U.S. Pat. Nos. 3,948,959; 3,845,156; 4,298,755; 4,355,176; 4,374,269, and elsewhere. The prior art is directed primarily to the reaction step in the preparation of methacrylic acid by oxydehydrogenation of isobutyric acid and there is little or no information in the prior art as to how to isolate pure methacrylic acid from the mixture which results from the oxydehydrogenation process. The effluent from the oxydehydrogenation of isobutyric acid usually contains methacrylic acid, unreacted isobutyric acid and may contain lesser amounts of other materials such as polymerization inhibitors, acetone, acetic acid, low polymers, and traces of other organic acids, aldehydes, ketones and hydrocarbons. The major impurity in such crude methacrylic acid is usually the isobutyric acid which can be present in from 100 ppm to 50 weight percent based on the methacrylic acid present. In most processes for the production of methacrylic acid by the oxydehydrogenation of isobutyric acid, the reactor effluent will contain from about 5 to 15% by weight of isobutyric acid.

The crystallization characteristics of methacrylic acid in the presence of some impurities have been studied by A. C. Konov, et al., *Tr. Khim. Khim. Teckhnol.* (4), 1973, pp. 59–60. The separation of mixtures of methacrylic acid and isobutyric acid by vacuum distillation has been described in U.S. Pat. No. 3,663,375 and Japanese Pat. No. 52 7917. The vacuum distillation method is costly in terms of energy used and loss of product caused by polymerization. Mixtures of methacrylic acid and isobutyric acid have been separated by the roundabout and expensive method involving esterification, distillation to separate the esters followed by hydrolysis of the methacrylate ester back to the desired methacrylic acid.

I have discovered a method for the purification of methacrylic acid from its substantially anhydrous mixtures with isobutyric acid and other possible trace materials, such as mixtures produced by oxydehydrogenation of isobutyric acid which involves the crystallization of methacrylic acid and its removal from said mixtures with recycle of the isobutyric acid back to the oxydehydrogenation reactor if desired.

My invention can be illustrated by reference to the accompanying drawing wherein the crude methacrylic acid to be purified is contained in a storage vessel 10 which may be supplied with the dehydrated effluent from an oxydehydrogenation reactor (not shown) in which isobutyric acid has been converted to methacrylic acid or other source. The crude substantially anhydrous methacrylic acid from 10 is fed through line 20 to a counter-current heat exchange unit 11 where it is cooled by melting solids produced in unit 13. This is an energy saving measure used to pre-cool stream 20. Additional heat exchange (not shown) of stream 20 can be done with stream 29 wherein stream 20 is further cooled and potential methacrylic acid crystal nuclei are formed.

Stream 20 after pre-cooling is fed to a refrigeration unit 12 where more heat is removed and crystals of methacrylic acid begin to form and usually are formed in from 30 to 40% by weight of the total liquid feed and can range up to about 60% in some cases. The resulting liquid-crystal slurry stream 21 is then separated in unit 13 which may be a single or staged separation unit which separates the solid from the liquid. In the particular case of a stream composed of 10% by weight of isobutyric acid and 90% by weight of methacrylic acid, the rate of crystallization is rapid and the crystals are purified, about 3 to 6 equivalent stages in unit 13 are required to obtain methacrylic acid having a maximum of 100 ppm isobutyric acid impurity in it. The process operations represented by 13 are (1) separation of mother liquor from the crystals which can be accomplished by filtration, etc., melting a portion of the separated crystals to form a melt, and (2) refluxing a portion of the melt in a counter-current fashion with the crystals to provide opportunity for the purification process to occur. Ordinarily such separation processes for solid/liquid separation are of longer duration than for liquid/vapor separation systems and the former may require residence times of as much as 10 hours but more likely 3 hours or less. Stream 22 is warmed by incoming stream 20 in heat exchange unit 11 to produce purified methacrylic acid stream 23 which may be all liquid or a slurry of solid plus liquid. The purified methacrylic acid in stream 23 is received in vessel 18.

The mother liquor produced in unit 13 which includes any rinsing or washing residue from the purified methacrylic acid melt refluxing and purification process is removed from unit 13 as stream 24 which is substantially enriched with isobutyric acid. In actual practice when stream 20 is composed of 10% by weight of isobutyric acid and 90% by weight of methacrylic acid and a 45% crystallization occurs in unit 13 with a 15% melt reflux with the effective stagewise distribution coefficient in units 12 and 13 of 0.05, the composition of stream 24 is 14.28% by weight of isobutyric acid. Stream 24 is admixed with stream 28 which is a slurry of solids plus liquids leaving separator 16. The temperature of stream 28 is sufficiently low (about −30° C.) to assure that the equilibrium concentration of the mother liquor in stream 27 and, consequently, the concentration of isobutyric acid in stream 29 is at the desired level for the most economic operation. The liquids in streams 27, 28 and 29 represent the maximum isobutyric acid concentration to be found in the process and it may range from 22 to 75 weight percent of isobutyric acid, but is more typically about 50% by weight. A temperature of about −30° C. when the isobutyric acid content is about 50% by weight is adequate so that when streams 24 and 28 are mixed more crystals of methacrylic acid will form in stream 25. Additional purification of the crystals can take place in units 14, 15 and 16, which units represent the secondary recovery section and represent one or more stages of separation. In the actual case described above, in which line 20 contains a mixture of 10% by weight of isobutyric acid and 90% by weight of methacrylic acid and in which waste stream 29 contains 50% by weight of isobutyric acid and 50% by weight of methacrylic acid, a per-pass requirement is from 2 to 4 separation stages.

Unit 14 provides separation of methacrylic acid crystals from mother liquor via one or more separational processes common to solid/liquid systems including gravitational, centrifugal and filtration techniques. Unit 17 provides for the melting of some crystals contained in unit 14, such that the melt can provide a relatively pure reflux to wash/rinse and purify the crystals. The combination of units 14, 15 and 16 provide a sufficient combination of residence time, crystal formation rate, crystal size and solid/liquid separation such as to provide one or more equivalent stages of separation.

An objective of this invention is to provide a purified product from unit 14 which is then combined with stream 20 so that the isobutyric acid concentration in the product from unit 14 is less than or equal to the isobutyric acid concentration in stream 20. As an option for energy conservation, the product from unit 14 which passes through melter 17 need not be completely melted but can be a slurry of solids/liquid which can be mixed with stream 20 to provide additional cooling.

The mother liquor from unit 14 as stream 26 is also cooled in unit 15 to produce a liquid/solids slurry. It is an object of this invention to provide adequate circulation in the stream loop 25, 26, 27 and 28 to maintain an easily handleable solid/liquid ratio and at the same time to obtain an isobutyric acid concentration which is high enough to be economical as feed to an oxydehydrogenation reactor (not shown) in which isobutyric acid has been converted to methacrylic acid or other source. The crude substantially anhydrous methacrylic acid from 10 is fed through line 20 to a counter-current heat exchange unit 11 where it is cooled by melting solids produced in unit 13. This is an energy saving measure used to pre-cool stream 20. Additional heat exchange (not shown) of stream 20 can be done with stream 29 wherein stream 20 is further cooled and potential methacrylic acid crystal nuclei are formed.

Stream 20 after pre-cooling is fed to a refrigeration unit 12 where more heat is removed and crystals of methacrylic acid begin to form and usually are formed in from 30 to 40% by weight of the total liquid feed and can range up to about 60% in some cases. The resulting liquid-crystal slurry stream 21 is then separated in unit 13 which may be a single or staged separation unit which separates the solid from the liquid. In the particular case of a stream composed of 10% by weight of isobutyric acid and 90% by weight of methacrylic acid, the rate of crystallization is rapid and the crystals are purified, about 3 to 6 equivalent stages in unit 13 are required to obtain methacrylic acid having a maximum of 100 ppm isobutyric acid impurity in it. The process operations represented by 13 are (1) separation of mother liquor from the crystals which can be accomplished by filtration, etc., melting a portion of the separated crystals to form a melt, and (2) refluxing a portion of the melt in a counter-current fashion with the crystals to provide opportunity for the purification process to occur. Ordinarily such separation processes for solid/liquid separation are of longer duration than for liquid/vapor separation systems and the former may require residence times of a means to recover isobutyric acid, stream 29, which can be recycled to other process steps, such as for additional feed to an oxydehydrogenation reactor unit.

Unit 16 is also characterized by means to preferentially direct polymerization inhibitor, such as hydroquinone, out of the system via stream 29 or removed via a filter or centrifuge as particulates (not shown) from stream 29 in the case in which isobutyric acid is preferentially less concentrated in inhibitor.

The purification process of this invention is also characterized in that it avoids much risk of loss of methacrylic acid by polymerization in that it keeps the heat source of the melters (11 and 17) at temperatures well below 100° C., and the heat is usually transferred only to inhibited liquids across the heat transfer surfaces and the warmed, inhibited liquids are then contacted directly with purified crystals of methacrylic acid so that the crystals melt. The pure melt liquids are mixed with the inhibited liquids to maintain suitable levels of inhibitor concentration in the final methacrylic acid product. In this manner, the heated liquids are maintained with more than adequate levels of inhibitor for extra protection against polymerization, yet the purified methacrylic acid product contains a desired level of inhibitor.

I claim:

1. The process for purification of methacrylic acid from its mixtures with isobutyric acid and other minor organic impurities said mixtures comprising the dehydrated effluent from an oxydehydrogeneration reactor in which isobutyric acid is oxydehydrogenated to methacrylic acid comprising
   A. precooling the methacrylic acid-isobutyric acid mixture;
   B. further cooling the mixture to a temperature in the range of from about 16° C. to −55° C. to cause from 30 to 60% by weight of the methacrylic acid to crystallize to form a slurry of methacrylic acid crystals and liquid;
   C. separating the methacrylic acid crystals from the slurry leaving behind the mother liquor, melting some of the crystals, refluxing a portion of the melt in a counter-current fashion with the crystals to effect purification and combining the melt with the mother liquor;
   D. melting the purified methacrylic acid crystals to form a slurry or melt and recovering the purified methacrylic acid.

2. The process of claim 1 wherein the methacrylic acid in A is a mixture containing from 100 ppm to 50% by weight of isobutyric acid.

3. The process of claim 2 wherein the initial cooling of the mixture in A is supplied by the melting which occurs 4. The process of claim 3 wherein the mother liquor from C which is rich in isobutyric acid is further purified as in steps B and C.

5. The process of claim 3 wherein the mother liquor from C is recycled to an oxydehydrogenation reactor to convert more isobutyric acid to methacrylic acid.

6. The process of claim 1 wherein methacrylic acid-isobutyric acid mixture in A contains from 5-15% by weight of isobutyric acid.

7. The process of claim 1 wherein an effective amount of a polymerization inhibitor is included in step C.

8. The process of claim 1 wherein an effective amount of a polymerization inhibitor is included in step D.

* * * * *